United States Patent [19]

Pappin et al.

[11] Patent Number: 5,071,909

[45] Date of Patent: Dec. 10, 1991

[54] IMMOBILIZATION OF PROTEINS AND PEPTIDES ON INSOLUBLE SUPPORTS

[75] Inventors: Darryl J. C. Pappin, West Concord; James M. Coull, Acton; Hubert Koester, Concord, all of Mass.

[73] Assignee: Millipore Corporation, Bedford, Mass.

[21] Appl. No.: 385,711

[22] Filed: Jul. 26, 1989

[51] Int. Cl.$^5$ ...................... C08G 63/91; C12N 11/04
[52] U.S. Cl. .................................... 525/54.1; 521/53; 530/812; 530/815; 530/817; 435/182
[58] Field of Search ............... 525/54.1; 530/812, 815, 530/817; 521/53; 435/182, 180

[56] References Cited

U.S. PATENT DOCUMENTS

| | | | |
|---|---|---|---|
| 4,169,014 | 9/1979 | Goldberg | 435/182 |
| 4,326,009 | 4/1982 | Royer | 428/407 |
| 4,737,544 | 4/1988 | McCain et al. | 525/54.1 |
| 4,757,014 | 7/1988 | Hendrickson et al. | 435/180 |
| 4,774,178 | 9/1988 | Egerer et al. | 435/41 |

OTHER PUBLICATIONS

Sequence from Picomole Quantities of Proteins Electroblotted onto Polyvinylidene Difluoride Membranes, Matsudaira JBC. 262, 10035 (1987).
Pappin, D. J. C. et al., *Anal. Biochem.* 187:10-19 (1990).
Tarr, G. E., *J. Protein Chem.* 7:293 (1988).
Aebersold, R. et al., *J. Biol. Chem.* 261:4229 (1986).
Coull, J. et al., in *Methods in Protein Sequencing Analysis* (1989), Wittman-Liebold, B. (Ed) Splinger-Verlag, Berlin.
Pappin, D. J. C. et al., Abstract *Protein Society* Meeting, Seattle, Wash., Jul. 29, 1989.

*Primary Examiner*—Thurman K. Page
*Assistant Examiner*—G. S. Kishori
*Attorney, Agent, or Firm*—Hamilton, Brook, Smith & Reynolds

[57] ABSTRACT

The invention pertains to a method for immobilizing proteins or peptides onto a flat, microporous membrane surface in a form suitable for sequence analysis or other chemical or enzymatic processes. The process involves the formation of a thin polymer network that entraps the protein or peptide therein.

30 Claims, 3 Drawing Sheets

IMMOBILIZATION OF PROTEINS AND PEPTIDES ON INSOLUBLE SUPPORTS

BACKGROUND OF THE INVENTION

Proteins and peptides are naturally occurring heteropolymers composed of amino acids. Proteins are found in all living cells and function as structural and transport elements, catalytic enzymes and hormones. The order of the amino acids in the protein chain (primary structure) ultimately determines the complex three dimensional solution structure adopted by a protein that is necessary for active biological function. Research directed towards the structure and function of particular proteins often requires that the primary structure (sequence) be determined.

Recently there has been considerable interest in sequencing proteins which are available in much smaller amounts. These proteins include growth factors, peptide hormones, cell membrane receptors and proteins involved in intracellular signal transduction. The complete primary structures of these low-abundance proteins is now frequently determined using combinations of protein chemical and recombinant DNA methods. High sensitivity protein sequencing is also employed in the identification and isolation of the coding gene from appropriate gene libraries (Ullrich, A. et al., *Nature* 313:756 (1985).

For more than thirty years the order of amino acids in a protein chain has been determined by stepwise chemical or enzymic processes in which single amino acids are selectively removed one by one from either the amino- or carboxy- terminal end. The preferred chemical degradation method was introduced by Edman (*Acta Chem. Scand.* 4:283 (1950), but other methods have been developed and can be usefully employed in other instances.

In the Edman process, the protein is first reacted at its amino terminus with an isothiocyanate (e.g., phenylisothiocyanate, PITC) under basic conditions to form the phenylthiourea. Treatment with anhydrous acid (e.g., trifluoracetic acid, TFA) causes cyclization of the phenylthiourea to the anilinothiazolinone with concomitant cleavage of the N-terminal amino acid from the polypeptide and exposure of the alpha amine of the next, adjacent amino acid in the chain. The free ATZ amino acid is extracted, converted to the more stable phenylthiohydantoin (PTH) derivative by treatment with aqueous acid (e.g., 20% v/v aqueous TFA) and identified by chromatographic means (e.g., reverse-phase high pressure liquid chromatography (HPLC) or thin-layer chromatography). The parent polypeptide, now shortened by one residue, is subjected to repeat reaction with PITC and TFA to furnish the next ATZ amino acid in sequence.

The repetitive nature of the process lends itself readily to automation, and several automated sequencing machines have been developed over the past 25 years, all implementing variations of the basic Edman degradation chemistry. Several of these machines are the liquid-phase sequencer developed by Edman and Begg (Edman. P., and Begg, G., *Eur. J. Biochem.* 1:20 (1967) and U.S. Pat. No. 3,725.010), the solid-phase sequencer (Laursen R., *Eur. J. Biochem.* 20:89 (1971) and the gas-phase sequencer (Hewick, R. M. et al., *J. Biol. Chem.* 256:7990 (1981)).

The solid-phase process described by Laursen is distinct from the gas- and liquid-phase implementations of the Edman chemistry in that the polypeptide sample is covalently immobilized to a solid support before being subjected to the degradation chemistry. Attractive advantages to this latter approach stem from the fact that proteins which are covalently linked to an insoluble matrix can readily be separated, without extractive losses, from reagent and reaction by-products. This leads directly to shorter instrument cycle times, higher stepwise sequencing efficiencies and significant reduction in the UV-absorbing background contaminants that can interfere with the identification of PTH amino acids by reverse-phase HPLC. The solid-phase approach also allows for considerable flexibility in the choice of reagents, solvents and reaction conditions necessary for the development of highly efficient sequencing chemistries (for review see Laursen, R. A. and Machleidt, W., in *Methods of Biochemical Analysis* 26:201 (1980)).

Numerous derivatized supports have been described for use in solid-phase sequence analysis, including polystyrene beads derivatized with both aryl and alkyl-primary amines (Laursen, R. A. *Eur. J. Biochem.* 20:89 (1971)), controlled pore glass beads derivatized with alkyl amines, aryl amines and diisothiocyanates (Wachter, E., et al., *FEBS Lett.* 35:97 (1973); Weetall, H. H., *Biochem. Biophys. Acta* 212:1 (1970)) and both glass fiber sheets and polyvinylidene difluoride membranes derivatized with diisothiocyanates (Aebersold, R., et al., *J. Biol. Chem.* 261:4229 (1986); Coull, J., et al., in *Methods in Protein Sequence Analysis* (1989) Wittman-Liebold, B., (Ed.) Springer-Verlag, Berlin). Proteins and peptides have been successfully covalently attached to all the above derivatized supports and analysed by solid-phase Edman degradation.

One feature of these classical approaches to achieving covalent attachment of proteins and peptides to an insoluble matrix was that the matrix surface itself was derivatized with chemical groups involved in the linking process. In a more unconventional approach, Tarr described a process whereby proteins or peptides could be covalently immobilized on the interior surfaces of glass capillaries by the formation of a polymer network comprised of protein and polyamine polymers covalently crosslinked with 1,4-phenylenediisothiocyanate (Tarr, G. E., *J. Protein Chem.* 7:293 (1988)). Tarr noted that with glass capillaries the resulting polymer network was effectively immobilized on the walls of the capillaries even in the absence of covalent linkages between the polymer network and the glass. This was not the case for plastic capillary surfaces, where the polymer network had to be covalently linked to the surface to prevent desorption from the tubing walls during the sequencing chemistry.

Incremental improvements in instrumentation and laboratory techniques over the past two decades (see Wittman-Liebold, B., (Ed.) in *Methods in Protein Sequence Analysis* (1989) Springer Verlag, Berlin) have resulted in automated sequencing machines which can routinely provide useful sequence information at the level of only a few picomoles of protein (Kent, S., et al., *BioTechniques* 5:314 (1987)).

The high-yield purification of such small amounts of protein in a form suitable for sequence analysis presents a considerable technical challenge to the protein chemist. The more traditional purification techniques involving gel permeation, thin-layer and ion-exchange chromatography have increasingly given way to narrow and microbore implementations of high-pressure liquid chromatography (e.g., size exclusion, ion-exchange and reverse-phase) (see Wilson, K. J. and Yuan, P. M. in *Protein Sequencing: A Practical Approach* (1989) Findlay, J. B. C. and Geisow, M., (Eds.) IRL Press, Oxford and New York). The extremely high resolving power of one- and two-dimensional polyacrylamide gel electrophoresis has also attracted recent attention, particularly when combined with the transfer of separated proteins from the acrylamide or agarose gel matrix to sheets of nitrocellulose, nylon or hydrophobic polymers ('Western' blotting).

Early efforts to recover proteins from the separating gel matrices by direct electroelution from gel slices often resulted in low sample recovery, protein degradation and amino-terminal blocking (Bhown, A. S., et. al., *Analyt. Biochem.* 103:184 (1980); Hunkapillar, M. W. and Lujan, E., in *Methods of Protein Microcharacterization*, (1986) Shively, J. E., (Eds.), Humana Press, Clifton, NJ). Protein samples recovered from gel slices in this fashion were often also contaminated with large quantities of SDS detergent and buffer salts, the removal of which was often tedious and associated with significant loss of material.

Conventional diffusion blotting from polyacrylamide gels to nitrocellulose or nylon sheets was easy to perform, but protein recoveries were often low, particularly for larger proteins coated with SDS (Lee, C. Y., et al., *Analt. Biochem.* 123:14 (1982)).

Following the initial study by Towbin, H. et al, (*Proc. Natl. Acad. Sci. USA* 76:4350 (1979), electrophoretic transfer of proteins from gels to a sheet matrix has become the most widely used technique for protein blotting as it offers highly efficient transfer of even high molecular weight proteins within a short period of time. Once electrophoretically transferred to the blotting support the non-covalently adsorbed proteins could be visualized by staining with conventional dyes such as Coomassie brilliant Blue, Ponceau S, India ink or Amido Black. Contaminating buffer salts and detergents could also be rinsed from the surface without removal of the bound proteins, particularly when using hydrophobic polymer membranes such as polyvinylidene difluoride (PVDF) as the blotting matrix (Pluskal, M., et al., *BioTechniques* 4:272 (1986)).

The traditional blotting membranes such as nitrocellulose or nylon are destroyed by exposure to organic solvents and are therefore unsuitable for use in the direct sequence analysis of electroblotted proteins. Aebersold, R., et al., (*J. Biol. Chem.* 261:4229 (1986)) pioneered the use of chemically modified glass-fiber sheets as blotting supports that could be used for direct sequence analysis in gas-phase sequencers (see also Vanderkerkhove, J., et al., *Eur. J. Biochem.* 152:9 (1985)). These supports, derivatized with primary amines, quaternary amines or quaternized ammonium polybases added significant protein binding capacity to the base glass-fiber sheets but proved difficult to prepare and gave great variance in performance between laboratories. Severe problems were also encountered in visualizing the transferred proteins as the chemically modified glass-fiber surfaces readily bound the common protein staining agents described above and hence prevent the proteins from being detected.

The use of PVDF membranes for electroblotting and direct sequence analysis by P. Matsudaira (*J. Biol. Chem.* 261:10035 (1987) overcame many of the problems associated with the coated glass-fiber supports. This membrane has now emerged as the preferred substrate for electroblotting/sequencing applications and improvements to the original method have already been reported (Xu, Q. and Shively. J. E., *Analyt. Biochem.* 170:19 (1988) Speicher, D. W. in *Techniques in Protein Chemistry*, (1989) Hugli, T., (Eds.), Academic Press, San Diego).

The base membrane material (polyvinylidene difluoride) is a teflon-like polymer which is both mechanically strong and chemically inert. Protein transfer to the membrane is straightforward. In addition, the surface of the membrane demonstrates high protein binding capacity (up to 170 $\mu g/cm^2$). A key advantage is the ability to stain and destain the membrane using general protein dyes. Sequence data has been obtained on proteins detected with Coomassie Blue, Amido Black and reverse staining with Ponceau S (LeGendre, N. and Matsudaira, P., *BioTechniques* 6:154 (1988)). A major restriction that has prevented more widespread acceptance of solid-phase sequencing methods has been that the beaded supports (polystyrene or controlled pore glass, described above) or the capillary immobilization method described by Tarr for solid-phase sequencing are not compatible with the more direct electroblotting methods now commonly used for the preparation of samples for sequence analysis.

Proteins bound to the surfaces of the primary or quaternary amine-modified glass fiber sheets or PVDF membranes are immobilized by non-covalent interactions between protein and surface. The interaction is primarily by hydrophobic and/or weak coulombic attraction. However, protein sequence analysis of samples on these supports could only be performed using adsorptive or gas-phase sequencing chemistries that did not require a covalent linkage between the protein and surface. In an effort to utilize some of the favorable characteristics of solid-phase sequence analysis described previously, Aebersold, R. et al. (*J. Biol. Chem.* 261:4229 (1986)) covalently immobilized proteins by electroblotting onto glass-fiber sheets derivatized with phenylenediisothiocyanate (DITC). Significant drawbacks to this use of the glass fiber paper include the non-optimal surface texture that does not allow for intimate contact with the gel and undistorted transfer of protein during the blotting process, the low protein binding capacity (7–10 ug/cm$^2$), and the fact that both the initial and repetitive sequencing yields for proteins electroblotted onto derivatized glass-fiber sheets decreases with a decreasing amount of protein applied (Yuen. S, et al., *Applied Biosystems User Bulletin* 24 (1986). This approach was significantly improved by Coull, J., et al., (*Methods in Protein Sequence Analysis* (1989), Wittman-Liebold, B., (Ed.), Springer-Verlag, Berlin; U.S. patent application Ser. No. 07/212,430, filed June 28, 1988. entitled "Membranes for Solid Phase Protein Sequencing") using PVDF membranes modified with diisothiocyanates and now a U.S. Pat. No. 5,011,861. Initial expectations that these approaches might lead both to increased blotting and sequencing efficiencies were only partially realized. The major disadvantages were the high cost of preparing diisothiocyanate derivatized membrane surfaces in sufficient quantity for electroblotting applications and the significant problems associated with staining the electroblotted proteins on the chemically modified surfaces.

SUMMARY OF THE INVENTION

This invention pertains to a method for immobilizing peptides or proteins onto a microporous, insoluble support by entrapment within a thin polymer network. According to the method of this invention, peptides or proteins are entrapped onto a flat, microporous membrane surface by adsorbing a peptide or protein and a polymer onto the surface of the membrane. The microporous membrane should be sufficiently porous to allow liquids and reagents to flow through it. The polymer and/or the peptide or protein have functionalized groups which are then crosslinked by means of a crosslinking agent or by photoactivation to thereby produce a polymer network which entraps the peptide or protein therein. The protein or peptide may be covalently linked to the crosslinked polymer network or may be effectively immobilized within the polymer mesh by means of physical entrapment. The peptide or protein and polymer can be simultaneously or sequentially adsorbed onto the membrane surface which can be coated with a crosslinking agent. The process provides an efficient and cost effective means of immobilizing proteins and peptides to a solid support for the determination of their primary sequence (by chemical or enzymatic degradation) or for other enzymatic or chemical processes.

DETAILED DESCRIPTION OF THE INVENTION

Figure 1:
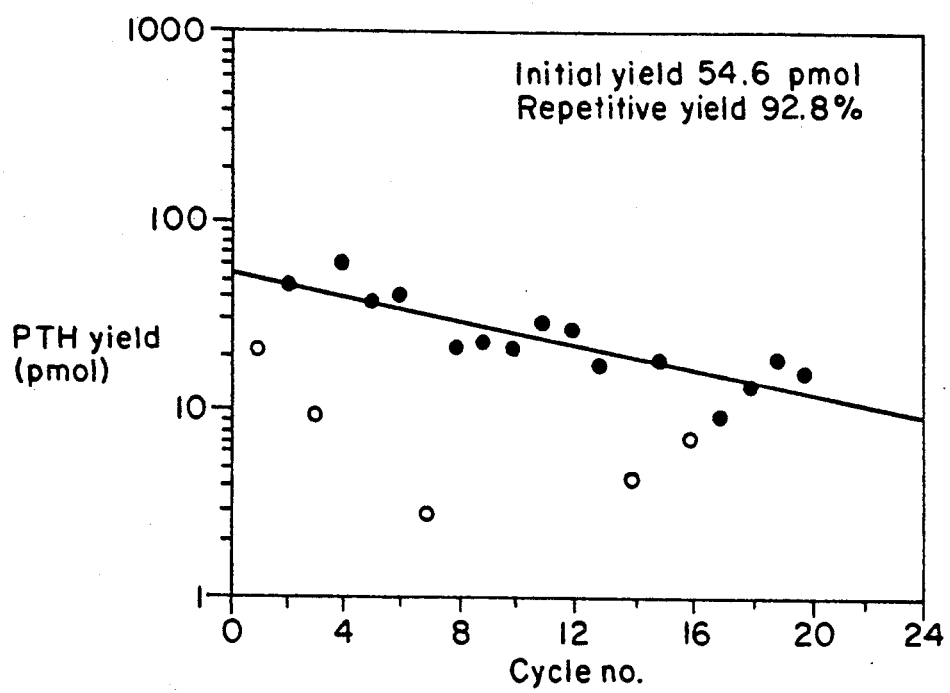
FIG. 1 shows solid-phase sequencing results of horse heart myoglobin electroblotted onto and then immobilized on PVDF membrane with a linear polyamine polymer and DITC.

This invention pertains to a method of immobilizing proteins and peptides onto a flat, microporous membrane surface in a form suitable for sequence analysis or other chemical or enzymatic processes. The process involves the formation of a thin polymer network that entraps a protein or peptide which is noncovalently adsorbed onto a flat membrane surface.

A peptide or protein and a polymer are adsorbed onto a flat membrane surface either simultaneously or sequentially. The polymer and/or the peptide or protein contain functional groups which can be crosslinked, to thereby form a polymer network which entraps the peptide or protein for subsequent sequencing or other chemical enzymatic processes. The protein or peptide may be covalently linked to the crosslinked polymer network or may be effectively immobilized within the polymer mesh by means of physical entrapment. In either case, the polymer network should not interfere with subsequent chemical or enzymatic processes.

The polymer network should effectively entrap the protein or peptide while still allowing for exposure of the protein and peptides to chemical reagents and solvents employed in sequencing or other chemical or enzymatic processes. The polymer network should also be capable of withstanding exposure to the chemical or enzymatic processes involved in protein sequencing.

The step of crosslinking can be achieved with a crosslinking agent or by photoactivation, such as by ultraviolet irradiation. When a crosslinking agent is used, it can be coated onto the surface of the membrane prior to depositing the peptide or protein and polymer thereon. Alternatively, the crosslinking agent can be deposited onto the membrane containing the peptide or protein and which can contain the polymer. In one embodiment, the protein or peptide, crosslinking agent and polymer can be admixed and simultaneously deposited onto the membrane.

The term "microporous membrane" is intended to include thin, flat, flexible sheets which have a uniform continuous porous structure that allows for solvents and reagents to flow through the membrane structure. The surface of the membrane can have different functional groups for covalent crosslinking to the polymer network. The membranes should be capable of withstanding both chemical and enzymatic protein sequencing processes. Several suitable membranes for solid-phase protein sequencing are described in U.S. patent application Ser. No. 07/212,430, filed June 28, 1988, U.S. Pat. No. 5,011,861 entitled "Membranes for Solid Phase Protein Sequencing", the teachings of which are incorporated herein by reference. Examples of suitable flat surfaces include porous membranes or sheets formed from various plastic materials (such as teflon, PVDF, nylon, cellulose acetate, nitrocellulose, polyester, polycarbonate, polysulphone or polystyrene), metals, zeolites, paper, silica, alumina or glass.

The protein or peptide entrapping system comprises three parts: a protein or peptide (P); a crosslinking agent (C); and a polymer (R). The sequence in which the three components are deposited onto the membrane can vary depending upon the functional groups to be crosslinked together. It should also be understood that when photoactivation is used to crosslink the polymer, there is no need to employ a crosslinking agent.

A protein or peptide (P) can be described as a polyfunctional molecule of formula (I):

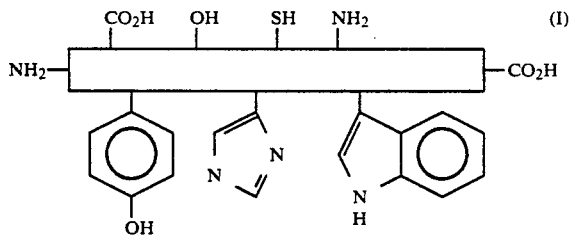

Each of the side-chain or terminal functionalities (e.g., amine, carboxyl, hydroxyl, thiol, phenol, imidazole, indole) may or may not be employed for the entrapping process. It should be noted however that the N-terminal amino group should preferably not be involved in the entrapping process as it needs to be available for the Edman degradation chemistry.

The crosslinking agent (C) has the general formula (II):

X and Y can be the same or different and may be selected from a variety of functional groups capable of reacting under appropriate conditions (known to those skilled in the art) with the polymer (R) and/or the polypeptide or protein (P). For example, X and Y can be selected from the following groups: —N=C=S; —N=C=O; —N=N=N; —COOH; —NH$_2$; —OH; —SH; —CO—A;

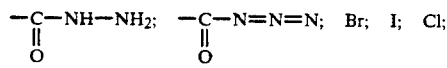

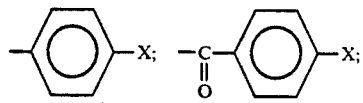

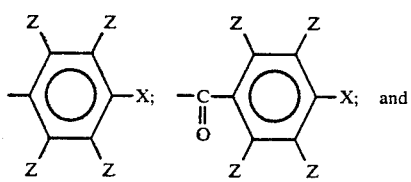

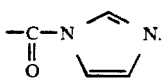

A is a carboxylic acid activating functionality (e.g. pentafluorophenoxy, p-nitrophenoxy, hydroxbenzotriazole, succinimidoyl or O-acyl urea). In addition to A, in situ derivatization of the carboxyl functionality with carbodiimide, for example may be employed.

Z can be selected from the group consisting of H, CH$_3$, C$_2$H$_5$, OH, I, Cl, Br, F, NO$_2$, SO$_3$, PO$_4$, and X where X is defined above.

L is a spacer group which can have different lengths and polarity and can be selected from (M)$_m$; (N)$_n$, and (O)$_o$; wherein M is a phenyl group; m is an integer from one to three; N is a linear or branched alkyl group, such as —CH$_2$, —CH(CH$_3$) —CH$_2$—, and —CH$_2$—CH$_2$—, n is an integer from one to 12; O is a linear or branched alkene, such as —CH=CH, —CH$_2$—CH=CH—

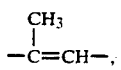

and o is an integer from one to 12.

L may also have the following general formulas (III, IV, V, VI, VII, VIII, IX, X, XI):

| | |
|---|---|
| (M$_m$—B—N$_n$)$_r$ | (III) |
| (N$_n$—B—N$_n$)$_r$ | (IV) |
| (M$_m$—B—M$_m$)$_r$ | (V) |
| (O$_o$—B—O$_o$)$_r$ | (VI) |
| (M$_m$—B—O$_o$)$_r$ | (VII) |
| (O$_o$—B—M$_m$)$_r$ | (VIII) |
| (O$_o$—B—N$_n$)$_r$ | (IX) |
| (N$_n$—B—O$_o$)$_r$ | (X) |
| (N$_n$—B—M$_m$)$_r$ | (XI) | wherein M, N, m and n are described above; r is an integer from one to 12; and B being selected from a variety of functionalities, such as: (M)$_m$, (N)$_n$, (O)$_o$, —O—, —S—, —S—S—, —NH—,

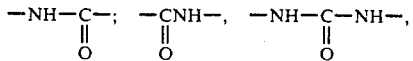

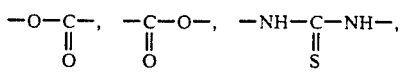

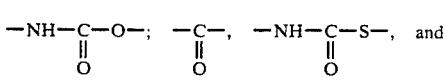

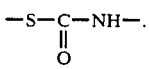

Although most of the time a bifunctional cross-linker (C) can be effectively used to entrap the protein or peptide (P), the invention is not limited to this, i.e. tri- or tetrafunctional crosslinking agents employing the above described functional groups and structural features can also be used.

Polymer (R) can be a large variety of polymers, both linear and branched, natural (e.g. proteins) and synthetic, with functional groups (X) as defined above may be used. R can be selected from a variety of monomeric units. Thus, R=(W)$_s$ where W is selected from:

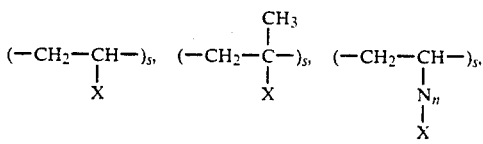

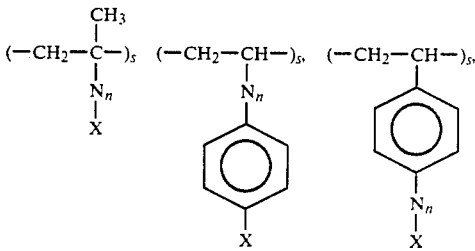

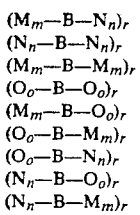 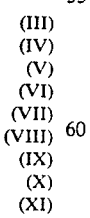

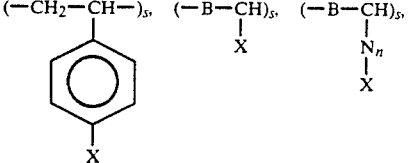

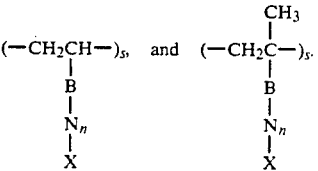

and s=1–2000; B and X are defined above.

Although the process of the invention works with linear polymers (R) as described above, branched polymers such as:

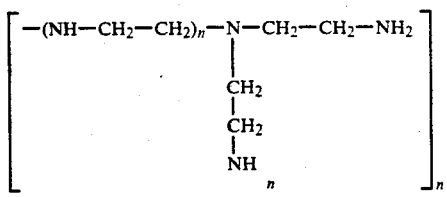

$$n = 1-2000$$

having primary, secondary and tertiary amino groups can be used (e.g. polyethyleneimine, PEI). The components C, R and/or P react together to form a three-dimensional polymer network, thereby entrapping the protein or peptide onto the flat, porous surface. The flat surface may be inert, or may be chemically derivatized with functional groups (X) as described above which allow for a covalent attachment of the three-dimensional polymer network to the flat surface.

The immobilization method of this invention can be used to determine the primary sequence of proteins or peptides. Proteins or peptides to be sequenced can be transferred from a separatory gel and adsorbed onto a microporous membrane surface either by direct blotting or by electroblotting. A polymer matrix is then formed according to the methods of this invention to thereby entrap the protein or peptide onto the surface of the membrane. The amino acid sequence of the immobilized protein or peptide is then determined on the solid phase using manual or automated solid-phase sequencing chemistries. The sequence of a peptide or protein can be determined by a stepwise chemical or enzymatic degradation from either the amino- or carboxy-terminal end. A preferred sequencing process is the Edman degradation method.

Proteins or peptides immobilized on a microporous membrane according to the methods of this invention can be used in a variety of applications which utilize immobilized proteins. For example, immobilized proteins can be used for enzymatic reactions, detection of antibodies, affinity separations, or as an immunoadsorbant. The immobilized proteins can also be used for both small and large scale solid-phase applications.

Covalent Immobilization of Proteins or Peptides to a PVDF Surface using Polyamine Polymers Crosslinked with 1,4-phenylenediisothiocyanate (DITC)

A very dilute PITC solution in a volatile solvent is first spotted onto the protein adsorbed onto a membrane surface, dried by evaporation and then allowed to react for a few minutes in a basic buffer to achieve partial modification of protein alpha- and epsilon amines as phenylthioureas. The protein is then overlayed, first with a solution of DITC (again in a volatile solvent) and then with a basic buffer containing a polyamine polymer (linear or branched), such as polyallylamine or polyethyleneimine and warmed to 40°-60° C. As the polymer solution dries onto the membrane surface, both the polymer and protein amino groups (alpha and epsilon) are covalently crosslinked by the formation of thiourea linkages to DITC. The protein is thus covalently entrapped within an extensive (but thin) polymer network that does not elute from the membrane surface during the sequencing chemistry. There may be some covalent linkage between the polymer amines and a PVDF surface (base-catalysed HF elimination followed by addition of amines into the double bonds), but alternatively the polymer network may be so large and conform so closely to the microscopic irregularities of the membrane surface that it remains totally immobilized. The partial modification of the protein N-terminus and lysine side-chains with PITC allows for the successful identification of these residues during sequencing.

The above procedure can be performed with the following variations. Instead of being electroblotted onto the PVDF membrane, a solution of protein may be spotted directly onto the membrane and dried down onto the surface by evaporation. Treatment with PITC solution, buffer, DITC solution and polymer solution is then performed as above. The polymer solution can be deposited before the DITC crosslinker, or alternatively, the protein can be dissolved in the polymer solution and spotted onto a clean membrane already pre-coated with PITC and DITC solutions as above. The crosslinking reaction then occurs as the polymer/protein solution dries out on the heated surface.

Both PITG and DITC are deposited on the membrane surface by the evaporation of the ethyl acetate, and rapid drying of the solvent is necessary to give an even coating. The choice of a suitable solvent is thus set by the requirement of a low boiling point (ethyl acetate, tetrahydrofuran and benzene work well). For an efficient crosslinking reaction to occur, both the buffer and polymer solutions should fully wet the dry PVDF surface, and thus must contain a percentage of organic modifier or other wetting agent. Preferably, the solvent is 50% v/v aqueous methanol because it has the ability to fully wet the dry PVDF surface and yet it will not dissolve either PITC or DITC from the membrane surface. This ensures that the even coating of isothiocyanates is maintained as the polyamine polymer dries down onto the surface where the crosslinking reaction occurs. The concentrations of PITC, DITC and polymer should be selected so as t maximize the amount of protein that can be covalently immobilized on the surface without forming a polymer layer of sufficient thickness to exclude protein material from exposure to the reagents of the sequencing chemistry or other enzymatic or chemical processes.

Covalent Immobilization of Proteins or Peptides to a PVDF Membrane Surface Using Polycarboxylic Acid Polymers Crosslinked with Bifunctional Arylamines In the case of proteins or peptides that contain no lysine residues, an alternative procedure can be employed to covalently entrap these molecules using the carboxylic acid groups at the C-terminus or the side-chains of aspartic acid and glutamic acid residues. In one embodiment of the process, a dilute solution of carbodiimide and bi-functional dianiline reagents (e.g., diisopropylcarbodiimide and methylenedianiline) in a volatile solvent (such as ethyl acetate or THF) is spotted onto protein non-covalently adsorbed onto a membrane surface. The solution is allowed to dry by evaporation, depositing the reagents on the surface. A second polymer solution containing a low concentration of a polycarboxylic acid polymer (linear or branched) e.g., polymethacrylic acid or polyacrylic acid, buffered to pH 4-6, is then spotted onto the membrane and allowed to dry by evaporation (20°-60° C.). Both the polymer and protein carboxyl groups are initially activated by the carbodiimide reagent to give O-acylureas which in turn react with the bi-functional dianiline reagent to yield stable amide linkages. The protein thus becomes covalently entrapped within a thin polymer film comprised of the polycarboxylic acid polymer and protein carboxyl groups crosslinked by the bi-functional dianiline reagent. At pH 4-6, the protein amino groups (alpha and epsilon) remain fully protonated and are thus essentially unreactive towards the activated carboxyl groups (important for the Edman sequencing chemistry) while the arylamine groups of the bi-functional dianiline compound are still available for the crosslinking reaction. As above, the conditions for immobilization can be altered such that the polymer may be deposited before the crosslinker or the protein may be dissolved in the polymer solution and evaporated onto a surface already coated with crosslinker and carbodiimide.

Covalent Immobilization of Proteins to a PVDF Membrane Surface Using Photoactivation In another embodiment of the invention, a dilute solution of polymer functionalized with a mixture of alkyl amines and phenyl azides or benzophenones is deposited by evaporation on a protein or peptide non-covalently adsorbed onto a membrane. The polymer coated membrane is then exposed to UV radiation, with concomittant generation of the nitrene radicals of the aryl azides or triplet diradicals of benzophenones. The free radicals react randomly with polymer alkyl amines as well as with various protein or peptide functional groups (amines, thiols, phenols, indoles, imidazoles, methylene groups). The protein is thus covalently entrapped within the three-dimensional polymer network for subsequent solid-phase sequence analysis. As above, the concentration of polymer should be chosen so as to maximize the amount of material available for sequencing. The protein or peptide may also be mixed with the polymer and co-deposited on the membrane surface before UV activation.

The invention will be further illustrated by the following non-limiting Examples.

EXAMPLE 1

Preparation of Protein Samples Electroblotted onto Polyvinylidene Difluoride (PVDF) Membranes 4 nmol samples of horse heart myoglobin (Type III; Sigma Chemical Co. or beta-lactoglobulin A (Applied Biosystems, Foster City, CA) were dissolved by heating at 95° C. for 3-5 minutes in 200 $\mu$l SDS sample buffer comprising 10% v/v glycerol, 2% w/v sodium dodecyl sulphate (SDS , 5% v/v 2-mercaptoethanol 0.002% w/v bromophenol blue and 60 mM Tris-HCL buffer pH 6.8. 10 $\mu$l aliquots, each containing 200 pmol protein, were then subjected to SDS polyacrylamide gel electrophoresis according to the method of Laemmli, U. K., (*Nature* 227:680 (1970)) [8 cm×7 cm gels, 0.75 mm thickness, 12% w/v acrylamide, 1:30 bis, gel and running buffers containing only 0.02% w/v SDS, electrophoresis for 200 V constant voltage for 30 minutes]. The gels were rinsed for 2-3 minutes by immersion in 25 mM Tris, 10% v/v methanol (pH 10.4) and the proteins then electroblotted onto Immobilon-P PVDF membranes (Millipore Corp., Bedford, MA) using the MilliBlot-SDE semi-dry electroblotting system (Millipore Corp., Bedford. MA) and the low-ionic discontinuous 6-aminohexanoic acid buffer system described by Svendsen, P. J. and Shafer-Nielsen, C., (*J. Biochem. Biophys. Methods* 3:97 (1980)). Transfer was accomplished by electroblotting at 1.5 mA/cm$^2$ of gel surface area for 45-60 minutes at constant current. The PVDF transfer membrane was then washed with distilled water (two changes of 200 ml, 10 minutes each, mild agitation), blotted dry with Whatman 3 mm filter paper and then thoroughly dried in vacuo for at least 20 min. The blotted proteins were visualized by immersing the dry membrane in a solution of 30% v/v methanol containing 0.5% w/v sulforhodamine B. The stained membrane was washed briefly with distilled water to remove excess dye and dried in vacuo for at least 20 minutes. The stained protein bands were then excised from the sheet using an 8 mm circular die punch or razor blade.

EXAMPLE 2

Solid-phase Sequence Analysis of Electroblotted Proteins Covalently Immobilized on PVDF Membrane with a Linear Polyamine Polymer and 1,4-phenylenediisothiocyanate (DITC)

A) An 8 mm disc of PVDF membrane with a sample of horse heart myoglobin electroblotted onto the membrane surface and stained with sulforhodamine B as in Example 1 was treated as follows. With the disc held at the edge with a pair of fine forceps, 10 $\mu$l of a solution of phenylisothiocyanate (PITC, 10 nmol/$\mu$l) in ethyl acetate was spotted onto both sides of the membrane disc and allowed to evaporate over 15-20 seconds. The disc was then placed on a mylar sheet lying on a metal heat-block at 55° C., 30 $\mu$l of a solution of 50% v/v methanol containing 2% v/v triethylamine pipetted onto the disc surface and the liquid droplet allowed to dry completely over 7-10 minutes. Again with the membrane disc held with a pair of forceps, 10 $\mu$l of 0.5% w/v DITC in ethyl acetate was applied to both sides and allowed to evaporate to dryness over 15-20 seconds. The disc was again placed on the mylar sheet heated to 55° C. and 30 $\mu$l of 50% v/v methanol containing 2% v/v triethylamine (TEA) and 0.1% w/v polyallylamine hydrochloride (low molecular weight, Aldrich Chemical Corp.) pipetted onto the surface. The solution was allowed to dry completely over 10 minutes and the polymer-coated membrane washed with methanol, distilled water and methanol to remove non-covalently bound material (both polymer and protein). The polymer-coated membrane disc was then placed directly in the reaction chamber of a MilliGen 6600 ProSequencer (Division of Millipore Corp., Burlington, MA) and subjected to 20 cycles of solid-phase Edman degradation as described by Laursen. R. A., et al. (*Methods in Protein Sequence Analysis*, (1989) Wittman-Leibold, B. (Ed.), p. 61, Springer-Verlag, Berlin).

All 20 residues of the test sample were readily identified, and the sequencing results are shown below (FIG. 1). The data from four such experiments on identical samples gave an average initial yield of 54.9 pmol with an average sequencing yield of 93.5% measured over the 20 cycles attempted.

In all of the Figures, the closed circles indicate residues used for regression analysis. The opened circles indicate residues (first, Ser, Thr, Cys, Trp, Lys) which are partially destroyed by coupling or sequencing procedures and not included in fitting of the line by regression analysis. The initial yield is derived from the intercept of the Y axis and the repetitive yield is calculated by taking the antilog of the slope of the fitted line.

Control experiments were also performed to demonstrate that the test protein was covalently immobilized on the membrane surface during the sequencing chemistry. In one control an identical sample of horse heart myoglobin electroblotted onto PVDF membrane and visualized as in Example 1 was placed directly into the sequencer reaction chamber and subjected to 20 cycles of Edman degradation. In two other controls, the above procedure was repeated on identical samples with the omission of either DITC crosslinker or the polyamine polymer. In all these cases no sequence was observed, with an experimental detection limit of approximately 500 fmol.

Figure 2:
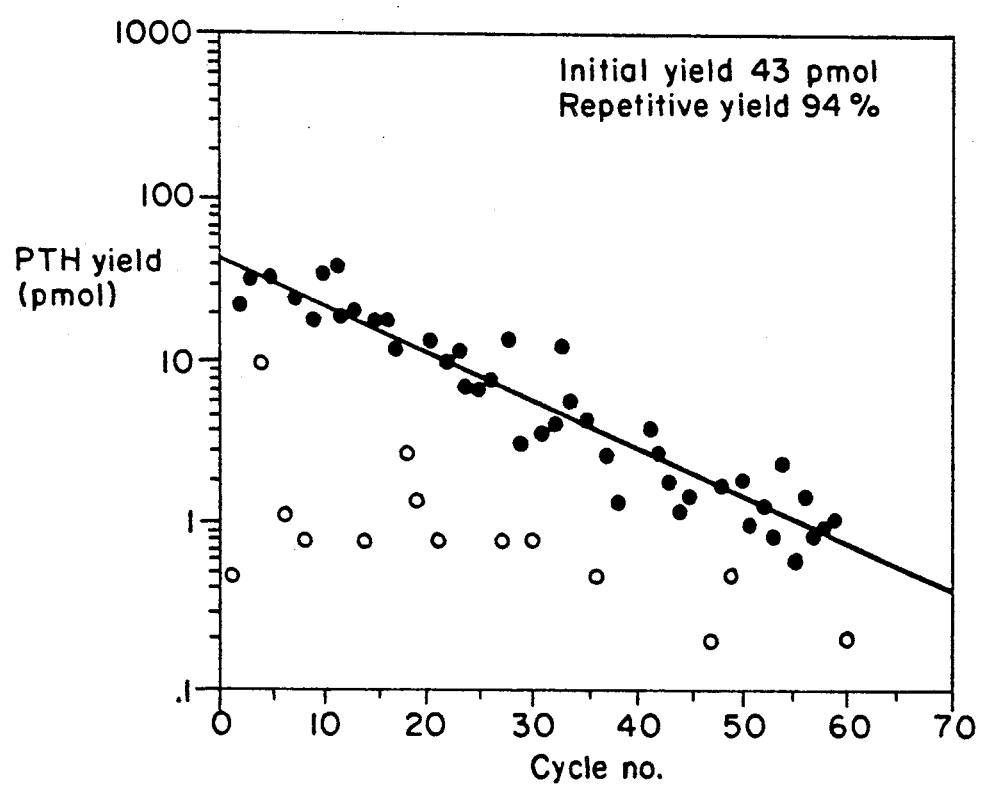
FIG. 2 shows solid-phase sequencing results of beta-lactoglobulin electroblotted onto the surface of a PVDF membrane and immobilized with a linear polyamine polymer and DITC.

B) An 3 mm disc of PVDF membrane with a sample of beta-lactoglobulin A electroblotted onto the surface and stained with sulforhodamine B as in Example 1 was treated with PITC, DITC and polyamine polymer solutions exactly as for Example 2A and subjected to 60 cycles of solid-phase Edman degradation as above. The sample give an initial yield of 43 pmol, and a repetitive sequencing yield of 94%. (FIG. 2).

EXAMPLE 3

Figure 3:
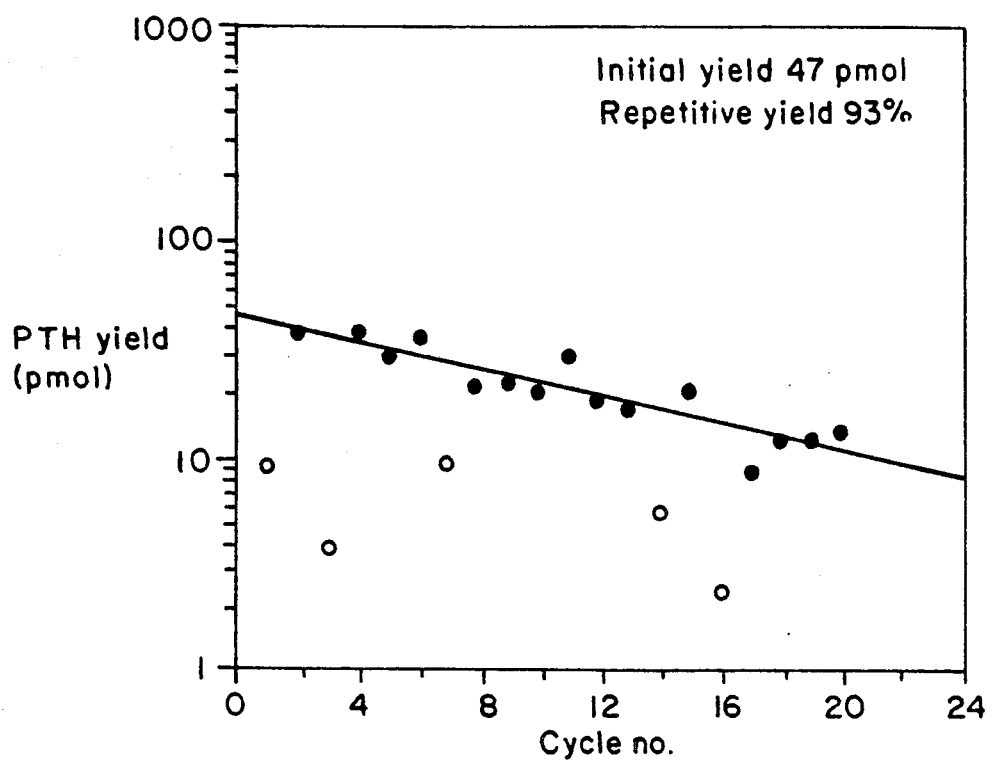
FIG. 3 shows solid-phase sequence data of electroblotted horse heart myoglobin immobilized on PVDF membrane with a branched polyamine polymer and DITC.

Solid-phase Sequence Analysis of Electroblotted Proteins Covalently Immobilized on PVDF Membrane with a Branched Polyamine Polymer and DITC An 8 mm disc of PVD membrane with a sample of horse heart myoglobin electroblotted onto the surface and stained with sulforhodamine B as in Example 1 was treated as follows. With the disc held at the edge with a pair of fine forceps, 10 μl of 0.5% w/v DITC in tetrahydrofuran (THF) was spotted onto both sides of the membrane disc and allowed to evaporate over 15–20 seconds. The disc was then placed on a mylar sheet resting on a metal heat-block at 55° C. and 30 μl of 0.1% w/v polyethyleneimine-18 (PEI-18; 1800 molecular weight) in 50% v/v aqueous methanol pipetted onto the surface. The liquid droplet was allowed to evaporate to dryness over 15 minutes, then the polymer-coated disc washed with methanol, water and methanol to remove non-covalently bound material. The disc was then subjected to 20 cycles of automated solid-phase Edman degradation as described above. Sequence data is displayed in FIG. 3. The sample gave an initial sequencing yield of 47 pmol and repetitive sequencing yield of 93%.

EXAMPLE 4

Figure 4:
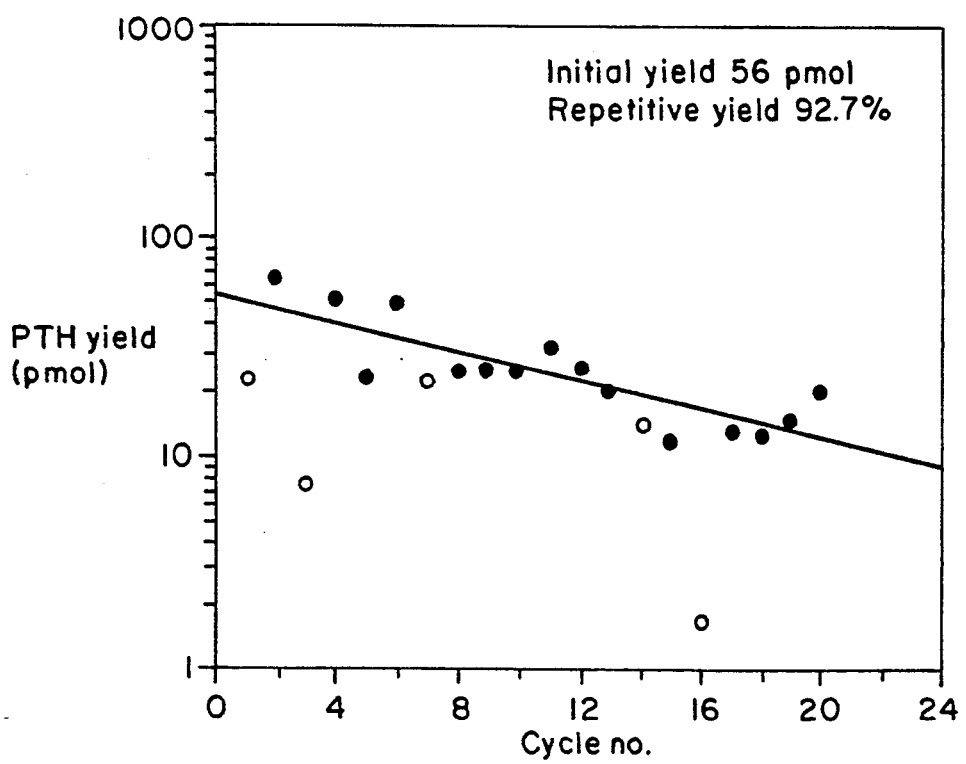
FIG. 4 shows solid-phase sequence data of horse heart myoglobin spotted onto PVDF membrane and immobilized using a linear polyamine polymer and DITC.

Solid-phase Sequence Analysis of Protein Spotted onto PVDF Membrane and Covalently Immobilized Using a Linear Polyamine Polymer and DITC 10 μl of water containing 200 pmol horse heart myoglobin was spotted onto a small (8 mm) disc of PVDF membrane previously wet by dipping in a solution of 50% v/v aqueous ethanol containing 5% v/v 4-methylmorpholine. The solution was dried by placing the membrane on a mylar sheet resting on a heat-block at 55° C. for 3–4 minutes. The non-covalently adsorbed protein was then covalently immobilized to the membrane surface by treatment with solutions of PITC, buffer, DITC and polyallylamine as described for Example 2A. The polymer coated membrane was washed with methanol, water and methanol and sequenced for 20 cycles by solid-phase Edman degradation as described above. The sample gave an initial sequencing yield of 56 pmol with a repetitive sequencing yield of 92.7% (FIG. 4).

EXAMPLE 5

Figure 5:
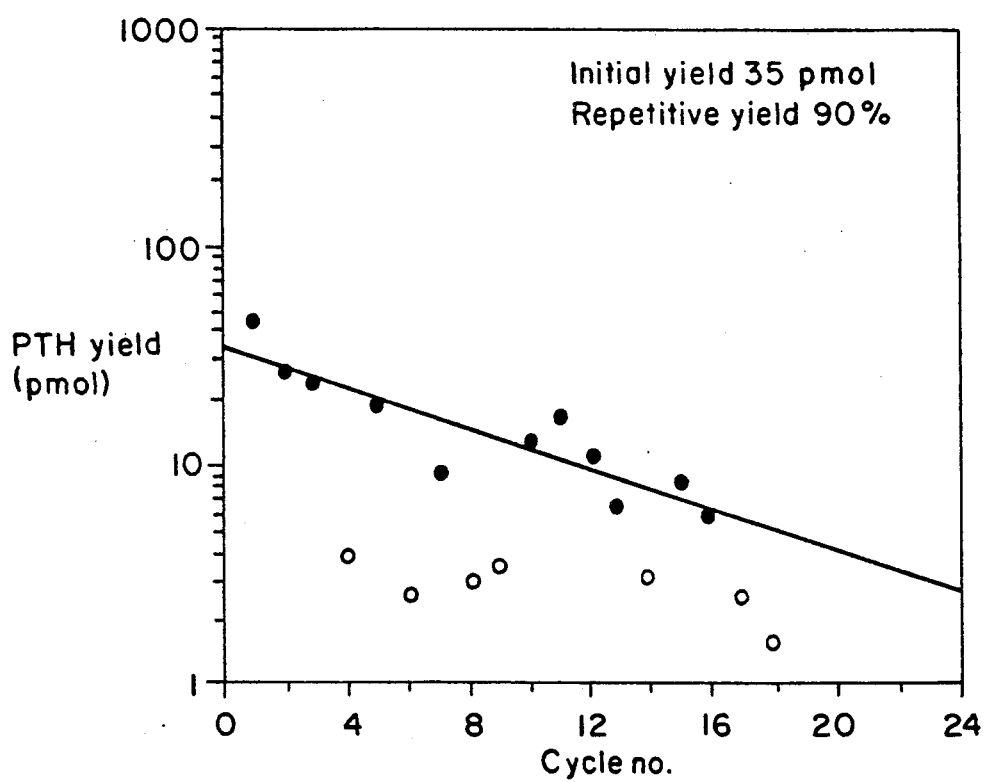
FIG. 5 shows solid-phase sequence data of electroblotted bovine beta-lactoglobulin A immobilized on PVDF membrane with a polycarboxylic acid polymer and methylenedianiline.

Solid-phase Sequence Analysis of Electroblotted Proteins Covalently Immobilized on PVDF Membrane with a Polycarboxylic Acid Polymer and Methylenedianiline An 8 mm disc of PVDF membrane with a sample of bovine beta-lactoglobulin A electroblotted onto the membrane surface and stained with sulforhodamine B as in Example 1 was treated as follows. With the membrane disc held by the edge with a pair of fine forceps, 10 μl of a solution of ethyl acetate containing 2% v/v diisopropylcarbodiimide and 0.5% w/v methylenedianiline was spotted onto both sides of the disc and allowed to evaporate to dryness over 15–20 seconds. The disc was placed on a mylar sheet resting on a heat-block at 55° C. and 30 μl of 50% v/v aqueous 1,4-dioxan containing 0.3% w/v polyacrylic acid (5,000 molecular weight) and 0.1 M tetrazole buffer pH 5 with n-methylmorpholine pipetted onto the surface. The liquid droplet was allowed to evaporate to dryness over 10 minutes, and the polymer-coated membrane then washed with methanol, water and methanol to remove unbound material. The washed disc was then subjected to 20 cycles of solid-phase Edman degradation as described above. The sequence data is shown in FIG. 5. The initial sequencing yield was 35 pmol and the repetitive yield 90%.

EXAMPLE 6

Solid-phase Sequence Analysis of Protein Covalently Immobilized on PVDF Membrane with Azido-polyethyleneimine Polymer A) Preparation of azido benzoid acid:

p-Aminobenzoic acid was treated with HBr and sodium nitrite in water to give the corresponding azidobenzoic acid in 72% yield. 82 mg recrystallized p-azidobenzoid acid dissolved in 2 ml anhydrous DMF and 90 mg carbonyldiimidazole added. The reaction to produce the activated imidazolide was allowed to proceed for 1 hour at room temperature in darkness and then the solution was added dropwise with vigorous stirring to a solution of 0.22 g PEI-150 (10,000 molecular weight) in 3 ml 70% v/v aqueous DMF. The solution was stirred for 1 hour at room temperature in darkness, then diluted 50-fold with 50% methanol to give a solution approximately 0.2% w/v azido-polymer. This solution was then treated with acetic acid dropwise to give a pH of approximately 5.

B) Immobilization of protein to PVDF membrane:

2 nmol of lyophilized horse heart myoglobin was dissolved in 100 μl (containing 300 pmol protein) spotted onto an 8 mm disc of PVDF membrane. The wet membrane was then exposed to shortwave UV light for 4 minutes to photoactivate the aryl azide groups and generate the corresponding nitrene species to achieve covalent crosslinking of both protein and polyamine chains. The polymer-coated disc was washed with methanol, water and methanol, then subjected to 12 cycles of solid-phase Edman degradation as described above. The protein gave an initial yield of 38 pmol and repetitive sequencing yield of 94%.

Equivalents

Those skilled in the art will know, or be able to ascertain using no more than routine experimentation, many equivalents to the specific embodiments described herein. These are intended to be encompassed by the following claims.

We claim:

1. A method of immobilizing a peptide or protein onto a flat, microporous membrane surface, comprising the steps of:
   a) adsorbing a peptide or protein onto the microporous membrane surface to noncovalently attach the peptide or protein thereto;
   b) depositing a polymer onto the adsorbed peptide or protein, wherein the polymer has functional groups which can be crosslinked; and
   c) crosslinking the polymer, to thereby produce a polymer network which entraps the peptide or protein therein, wherein the network does not interfere with subsequent chemical or enzymatic analysis of the protein or peptide.

2. The method of claim 1, further comprising crosslinking the peptide or protein to the polymer network to thereby entrap the peptide or protein by covalent linkage thereto.

3. The method of claim 1, wherein the peptide or protein is physically entrapped within the polymer network.

4. The method of claim 1, wherein the microporous membrane surface is selected from the group consisting of teflon, polyvinylidene difluoride, nylon, cellulose acetate, nitrocellulose, polyester, polycarbonate, polysulphone, polystyrene, metals, zeolites, paper, silica, alumina and glass.

5. The method of claim 4, wherein the microporous membrane surface is polyvinylidene difluoride.

6. The method of claim 1, wherein the polymer is selected from the group consisting of polyethyleneimine, polyvinylamine, polyallylamine, polyacrylic acid and polymethacrylic acid.

7. The method of claim 1, wherein the polymer is crosslinked by a crosslinking agent or by photoactivation.

8. The method of claim 7, wherein the crosslinking agent is selected from the group consisting of methylenedianiline, ethylenedianiline, diaminostilbene and 1,4-phenylenediisothiocyanate.

9. The method of claim 7, wherein the photoactivation is by UV radiation.

10. The method of claim 1, wherein the microporous membrane surface is coated with a crosslinking agent before adsorbing the peptide or protein and polymer thereon.

11. A method of immobilizing a peptide or protein onto a flat, microporous membrane surface, comprising the steps:
    a) adsorbing a peptide or protein onto a polyvinylidene difluoride membrane surface to noncovalently attach the peptide or protein thereto;
    b) depositing a polyamine polymer onto the adsorbed peptide or protein, wherein the polyamine polymer has functional groups which can be crosslinked; and
    c) crosslinking the polyamine polymer with 1,4-phenylenediisothiocyanate, to thereby produce a polymer network which entraps the peptide or protein therein, wherein the network does not interfere with subsequent chemical or enzymatic analysis of the protein or peptide.

12. The method of claim 11, further comprising crosslinking the peptide or protein to the polymer network to thereby entrap the peptide or protein by covalent linkage thereto.

13. The method of claim 11, wherein the peptide or protein is physically entrapped within the polymer network.

14. The method of claim 11, wherein the microporous membrane is coated with 1,4-phenylenediisothiocyanate before adsorbing the peptide or protein and polymer thereon.

15. The method of claim 11, wherein the polyamine polymer is polyallylamine.

16. A method of immobilizing a peptide or protein onto a flat, microporous membrane surface, comprising the steps of:
    a) adsorbing a peptide or protein onto a polyvinylidene difluoride membrane surface to noncovalently attach the peptide or protein thereto;
    b) depositing a polycarboxylic acid polymer onto the adsorbed peptide or protein, wherein the polycarboxylic acid polymer has functional groups which can be crosslinked; and
    c) crosslinking the polycarboxylic acid polymer with a dianiline crosslinking agent, to thereby produce a polymer network which entraps the peptide or protein therein, wherein the network does not interfere with subsequent chemical or enzymatic analysis of the protein or peptide.

17. The method of claim 16, further comprising crosslinking the peptide or protein to the polymer network to thereby entrap the peptide or protein by covalent linkage thereto.

18. The method of claim 16, wherein the peptide or protein is physically entrapped within the polymer network.

19. The method of claim 16, wherein the microporous membrane is coated with the dianiline crosslinking agent before adsorbing the peptide or protein and polymer thereto.

20. The method of claim 16, wherein the polycarboxylic acid polymer is polyacrylic acid or polymethacrylic acid.

21. A method of immobilizing a peptide or protein onto a flat, microporous membrane surface, comprising the steps of:
    a) adsorbing a peptide or protein onto a polyvinylidene difluoride membrane surface to noncovalently attach the peptide or protein thereto;
    b) depositing an azidopolymer or benzophenone polymer onto the adsorbed peptide or protein, wherein the polymer has functional groups which can be crosslinked; and
    c) crosslinking the azidopolymer or benzophenone polymer by exposing the microporous membrane to ultraviolet radiation, to thereby produce a polymer network which entraps the peptide or protein therein, wherein the network does not interfere with subsequent chemical or enzymatic analysis of the protein or peptide.

22. The method of claim 21, further comprising crosslinking the peptide or protein to the polymer network to thereby entrap the peptide or protein by covalent linkage thereto.

23. The method of claim 21, wherein the peptide or protein is physically entrapped within the polymer network.

24. A method of immobilizing a peptide or protein onto a flat, microporous membrane surface, comprising the steps of:

a) adsorbing a peptide or protein and a polymer onto the microporous membrane surface to noncovalently attach the peptide or protein thereto;

b) treating the adsorbed peptide or protein with phenylisothiocyanate (PITC) and subsequently treating the adsorbed protein or peptide with a base;

c) treating the product of step (b) with 1,4-phenylene diisothiocyanate (DITC);

d) depositing a polymer onto the adsorbed peptide or protein of step (c), wherein the polymer has functional groups which can be crosslinked; and e) crosslinking the polymer, to thereby produce a polymer network which entraps the peptide or protein therein, wherein the network does not interfere with subsequent chemical or enzymatic analysis of the protein or peptide.

25. The method of claim 24, wherein the microporous membrane surface is selected from the group consisting of teflon, polyvinylidene difluoride, nylon, cellulose acetate, nitrocellulose, polyester, polycarbonate, polysulphone, polystyrene, metals, zeolites, paper, silica, alumina and glass.

26. The method of claim 25, wherein the microporous membrane surface is polyvinylidene difluoride.

27. The method of claim 24, wherein the polymer is selected from the group consisting of polyethyleneimine, polyvinylamine, polyallylamine, polyacrylic acid and polymethacrylic acid.

28. The method of claim 24, wherein the polymer is crosslinked by a crosslinking agent or by photoactivation.

29. The method of claim 28, wherein the crosslinking agent is selected from the group consisting of methylenedianiline, ethylenedianiline, diaminostilbene and 1,4-phenylenediisothiocyanate.

30. The method of claim 24, wherein the microporous membrane surface is coated with a crosslinking agent before adsorbing the peptide or protein and polymer thereon.

* * * * *